(12) United States Patent
Hoshino

(10) Patent No.: US 8,742,159 B2
(45) Date of Patent: Jun. 3, 2014

(54) FLUORINATED COMPOUND AND FLUORINATED POLYMER

(75) Inventor: Taiki Hoshino, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 7 days.

(21) Appl. No.: 13/616,024

(22) Filed: Sep. 14, 2012

(65) Prior Publication Data

US 2013/0005924 A1    Jan. 3, 2013

Related U.S. Application Data

(63) Continuation of application No. PCT/JP2011/058321, filed on Mar. 31, 2011.

(30) Foreign Application Priority Data

Apr. 1, 2010  (JP) ................................. 2010-085028

(51) Int. Cl.
*C07C 69/70*    (2006.01)

(52) U.S. Cl.
USPC ............... 560/87; 560/104; 560/111; 560/66; 570/127; 526/247

(58) Field of Classification Search
USPC ........ 560/87, 104, 111, 66; 570/127; 526/247
See application file for complete search history.

(56) References Cited

U.S. PATENT DOCUMENTS

| 4,717,757 A | 1/1988 | Dubois et al. |
| 5,087,672 A | 2/1992 | Babirad et al. |
| 5,814,378 A * | 9/1998 | Onishi et al. ................... 428/1.3 |
| 7,276,623 B2 * | 10/2007 | Harada et al. ................. 560/129 |
| 8,324,314 B2 * | 12/2012 | Brown et al. .................. 524/590 |
| 2012/0165487 A1 * | 6/2012 | Hoshino ....................... 526/246 |
| 2012/0184695 A1 * | 7/2012 | Hoshino ....................... 526/242 |
| 2012/0190809 A1 * | 7/2012 | Hoshino ....................... 526/246 |

FOREIGN PATENT DOCUMENTS

| JP | 62-240307 | 10/1987 |
| JP | 63-048383 | 3/1988 |
| JP | 05-507483 | 10/1993 |
| JP | 09-020720 | 1/1997 |
| WO | WO 02/083809 | 10/2002 |
| WO | WO 2004/035708 | 4/2004 |

OTHER PUBLICATIONS

U.S. Appl. No. 13/718,194, filed Dec. 18, 2012, Hoshino.
International Search Report issued Apr. 26, 2011 in PCT/JP2011/058321 filed Mar. 31, 2011.

* cited by examiner

*Primary Examiner* — Peter D. Mulcahy
*Assistant Examiner* — Henry Hu
(74) *Attorney, Agent, or Firm* — Oblon, Spivak, McClelland, Maier & Neustadt, L.L.P.

(57) ABSTRACT

To provide a fluorinated compound having an $R^F$ group with at most 6 carbon atoms, whereby a fluorinated polymer having a highly durable water/oil repellency can be produced, and an environmental load is little, and a fluorinated polymer having a highly durable water/oil repellency and presenting little environmental load, obtainable by polymerizing such a fluorinated compound. A fluorinated compound represented by the following formula (I) and its polymer:

$$CH_2=C(M)COOXPhCOO(CH_2)_m C_r F_{2r+1} \quad (I)$$

(in the formula (I), M is a hydrogen atom, a methyl group or a halogen atom, X is $CHR^1CH_2O$ or $CH_2CHR^1O$, $R^1$ is a $C_{1-4}$ linear or branched alkyl group or $CH_2OR^2$, $R^2$ is a $C_{1-4}$ linear or branched alkyl group, Ph is a phenylene group, m is an integer of from 1 to 4, and r is an integer of from 1 to 6).

5 Claims, No Drawings

FLUORINATED COMPOUND AND FLUORINATED POLYMER

TECHNICAL FIELD

The present invention relates to a novel fluorinated compound and a fluorinated polymer obtainable by polymerizing it.

BACKGROUND ART

As a technique to simultaneously impart water repellency and oil repellency to a surface, it is known to treat an article with an organic solvent solution or aqueous dispersion of a polymer comprising polymerized units of a polymerizable monomer containing a polyfluoroalkyl group (a group having a structure wherein at least two and at most all of hydrogen atoms in an alkyl group are substituted by fluorine atoms, such a polyfluoroalkyl group will be hereinafter referred to as an "$R^f$ group") in its molecule, or a copolymer of such a monomer with another monomer.

Such water/oil repellency is attributable to formation of "a low surface energy surface" having a low critical surface tension on the surface due to a surface orientation of $R^f$ groups on the coating film. It has been taken for granted that in order to attain both water repellency and oil repellency, orientation of $R^f$ groups at the surface is important, and in order to realize the surface orientation of $R^f$ groups, it is necessary to have constituting units derived from a monomer having a perfluoroalkyl group (a group having a structure wherein all of hydrogen atoms in an alkyl group are substituted by fluorine atoms, such a perfluoroalkyl group will be hereinafter referred to as an "$R^F$ group") with at least 8 carbon atoms in the polymer.

However, recently, EPA (Environmental Protection Agency in U.S.A.) has pointed out that a compound having an $R^F$ group with at least 8 carbon atoms is likely to be decomposed in vivo and in the environment, and the decomposed product is likely to be accumulated, i.e. its environment load is high. Therefore, a copolymer for a water/oil repellent composition is required, which has structural units derived from a monomer having an $R^F$ group with at most 6 carbon atoms and containing no structural units derived from a monomer having an $R^F$ group with at least 8 carbon atoms.

However, in the case of a monomer having an $R^f$ group with at most 6 carbon atoms, as compared with a monomer having an $R^f$ group with at least 8 carbon atoms, the $R^f$ orientation at the surface tends to be weak, and the water/oil repellency tends to be low. It is known to increase the water/oil repellency even in the case of a monomer having an $R^f$ group with at most 6 carbon atoms, by copolymerizing it with a monomer not having an $R^f$ group and having a high microcrystallite melting point (Patent Document 1), or copolymerizing it with a monomer having a crosslinkable functional group and not having an $R^f$ group (Patent Document 2).

On the other hand, with a polymer composed solely of a monomer having an $R^f$ group with at most 6 carbon atoms, it has been so far impossible to impart a sufficient water/oil repellency and excellent durability thereof.

Therefore, with respect to a monomer having an $R^f$ group with at most 6 carbon atoms, particularly an $R^F$ group with at most 6 carbon atoms, a monomer and its polymer have been desired, whereby by polymerizing such a monomer, it is possible to obtain a polymer having a highly durable water/oil repellency.

PRIOR ART DOCUMENTS

Patent Documents

Patent Document 1: WO02/083809
Patent Document 2: WO04/035708

DISCLOSURE OF INVENTION

Technical Problem

It is an object of the present invention to provide a fluorinated compound having an $R^F$ group with at most 6 carbon atoms, whereby a fluorinated polymer having a highly durable water/oil repellency can be produced, and an environmental load is little, and a fluorinated polymer having a highly durable water/oil repellency and presenting little environmental load, obtainable by polymerizing such a fluorinated compound.

Solution to Problem

The present invention provides a fluorinated compound represented by the following formula (I):

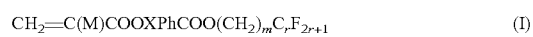

$$CH_2=C(M)COOXPhCOO(CH_2)_m C_r F_{2r+1} \qquad (I)$$

(in the formula (I), M is a hydrogen atom, a methyl group or a halogen atom, X is $CHR^1CH_2O$ or $CH_2CHR^1O$, $R^1$ is a $C_{1-4}$ linear or branched alkyl group or $CH_2OR^2$, $R^2$ is a $C_{1-4}$ linear or branched alkyl group, Ph is a phenylene group, m is an integer of from 1 to 4, and r is an integer of from 1 to 6).

The present invention further provides a fluorinated polymer obtainable by polymerizing at least one member selected from the above fluorinated compound of the present invention.

Advantageous Effects of Invention

By using the fluorinated compound of the present invention, it is possible to produce a fluorinated polymer having a highly durable water/oil repellency and presenting little load to the environment. Further, the fluorinated polymer of the present invention has a highly durable water/oil repellency and presents little load to the environment.

DESCRIPTION OF EMBODIMENTS

Now, embodiments of the present invention will be described. In this specification, a (meth)acrylate means an acrylate or a methacrylate. Likewise, (meth)acrylic acid means acrylic acid or methacrylic acid.

<Fluorinated Compound of the Present Invention>

The fluorinated compound of the present invention is a fluorinated compound which, as shown in the following formula (I), has an acryloyloxy group (which may be substituted) as a polymerizable group at its one terminal and an $R^F$ group with at most 6 carbon atoms at the other terminal and which has, as a bivalent linking group to link the two, a linking group containing one benzene ring directly connected to the ester bond. A fluorinated polymer obtainable by polymerizing the fluorinated compound of the present invention having such a molecular structure, has a water/oil repellency and also has a high durability whereby the water/oil repellency will not be impaired by e.g. use for a long period of time.

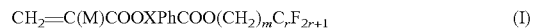

$$CH_2=C(M)COOXPhCOO(CH_2)_m C_r F_{2r+1} \qquad (I)$$

(in the formula (I), M is a hydrogen atom, a methyl group or a halogen atom, X is $CHR^1CH_2O$ or $CH_2CHR^1O$, $R^1$ is a $C_{1-4}$ linear or branched alkyl group or $CH_2OR^2$, $R^2$ is a $C_{1-4}$ linear or branched alkyl group, Ph is a phenylene group, m is an integer of from 1 to 4, and r is an integer of from 1 to 6).

In the above formula (I), M is a hydrogen atom, a methyl group or a halogen atom, specifically a halogen atom such as F, Cl or Br, but preferred M is a hydrogen atom or a methyl group, and more preferred M is a methyl group. In a case where M is a hydrogen atom, the obtainable polymer has water/oil repellency and is excellent in durability for maintaining such water/oil repellency. In a case where M is a methyl group, the obtainable polymer is particularly excellent in the initial water/oil repellency and excellent also in the durability for maintaining it.

In the above formula (I), X is $CHR^1CH_2O$ or $CH_2CHR^1O$. $R^1$ is a $C_{1-4}$ linear or branched alkyl group or $CH_2OR^2$. The $C_{1-4}$ linear or branched alkyl group may be specifically a methyl group, an ethyl group, a n-propyl group, an iso-propyl group, a n-butyl group, an iso-butyl group, a sec-butyl group or a tert-butyl group. $R^2$ is a $C_{1-4}$ linear or branched alkyl group, and $CH_2OR^2$ may be specifically $CH_2OCH_3$, $CH_2OCH_2CH_3$, $CH_2OCH(CH_3)_2$, $CH_2OC(CH_3)_3$, $CH_2OCH_2CH_2CH_3$, $CH_2OCH(CH_3)CH_2CH_3$ or $CH_2OCH_2CH(CH_3)CH_3$. $R^1$ is preferably a methyl group, an ethyl group or $CH_2OC(CH_3)_3$, particularly preferably a methyl group. In a case where $R^1$ is a methyl group, the obtainable polymer is particularly excellent in the initial water/oil repellency and excellent also in the durability for maintaining it.

In the above formula (I), Ph is a phenylene group. The phenylene group may be any of a 1,2-phenylene group, a 1,3-phenylene group and a 1,4-phenylene group, and in the present invention, Ph is preferably a 1,4-phenylene group in that hydrophilic ester groups are present apart from each other.

Further, in the above formula (I), m is an integer of from 1 to 4, but a preferred number of m is from 1 to 3. When the number of m is from 1 to 3, the raw material is readily available, such being desirable. Further, in the above formula (I), r is an integer of from 1 to 6. When r is within a range of from 1 to 6, the obtainable polymer exhibits water/oil repellency. However, in order to obtain higher water/oil repellency, r is preferably from 2 to 6, more preferably from 4 to 6.

In the present invention, among fluorinated compounds represented by the above formula (I), a fluorinated compound represented by any one of the following formulae (I-1) to (I-6) and (I'-1) to (I'-6) is preferred, and a fluorinated compound represented by any one of the following formulae (I-1) to (I-6) is particularly preferred.

(I-1)

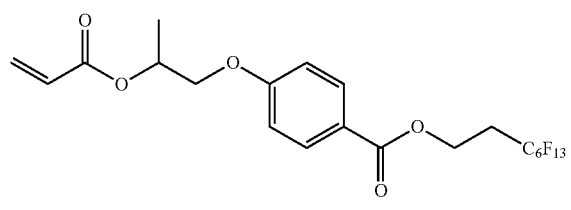

(I-2)

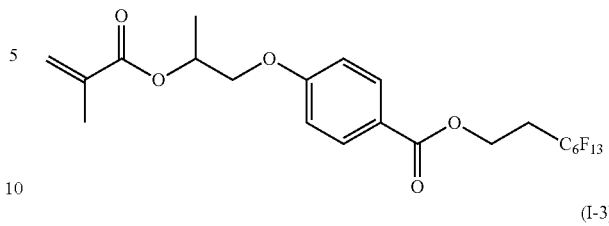

(I-3)

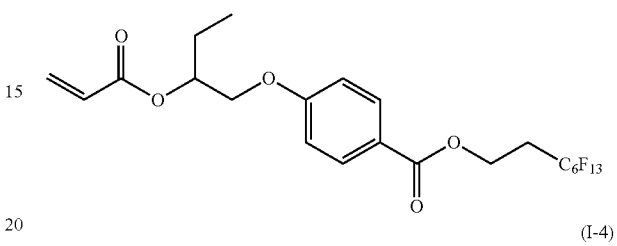

(I-4)

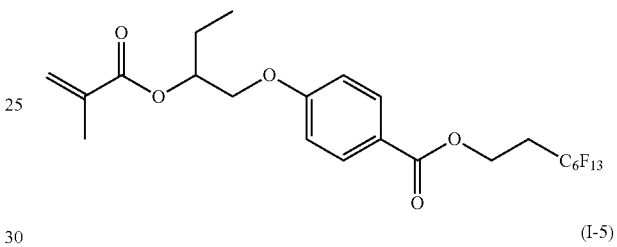

(I-5)

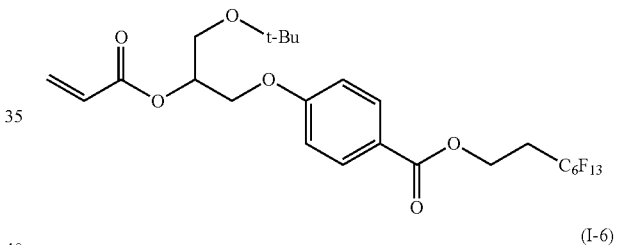

(I-6)

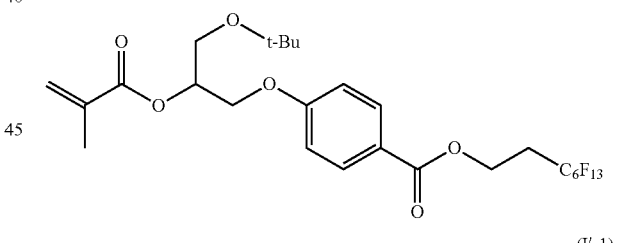

(I'-1)

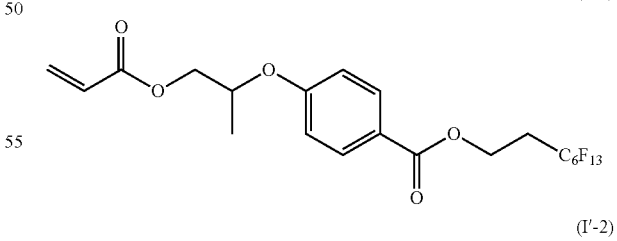

(I'-2)

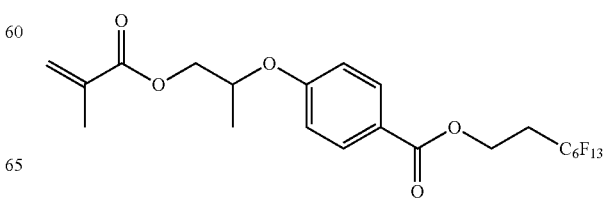

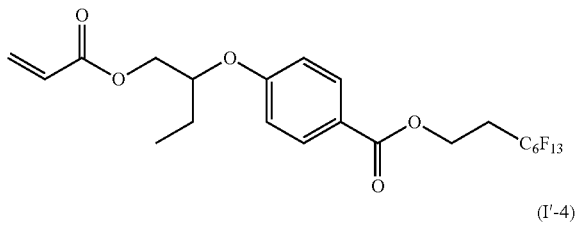

(I'-3)

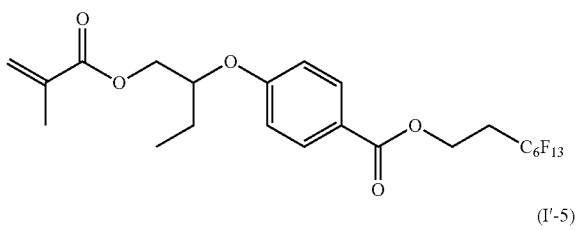

(I'-4)

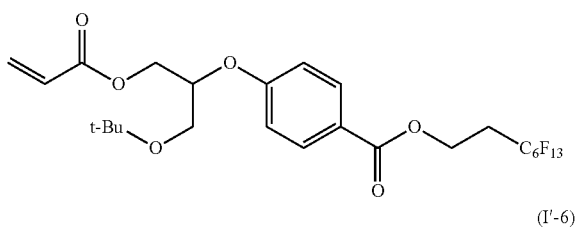

(I'-5)

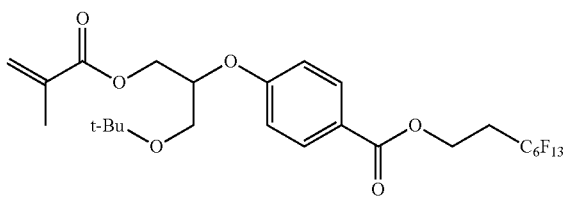

(I'-6)

<Production Method>

In the present invention, a method for producing the fluorinated compound represented by the above formula (I) (hereinafter referred to as fluorinated compound (I)) is not particularly limited.

Method for Producing Fluorinated Compounds (I) and (i')

The above fluorinated compounds (I) and (i') can be produced, for example, by carrying out reactions 1 to 3 which will be described below, although not limited thereto.

<Reaction 1>

Using, as a starting material, a compound represented by the formula HOPhCOOY$^1$ (wherein Y$^1$ is a hydrogen atom or a $C_{1-4}$ alkyl group), a compound (A) is obtained by reacting a compound having an R$^F$ group (perfluoroalkyl group) with at most 6 carbon atoms thereto, as shown by the following reaction formula.

HOPhCOOY$^1$+C$_r$F$_{2r+1}$(CH$_2$)$_m$OH→HOPhCOO(CH$_2$)$_m$C$_r$F$_{2r+1}$ (A)

In the above reaction 1, it is preferred to use 4-toluenesulfonic acid monohydrate, sulfuric acid or the like as a catalyst. The reaction 1 is carried out without solvent or in a solvent, and such a solvent may, for example, be specifically toluene or 2-butanone.

Specifically, the reaction 1 is carried out under the following preferred reaction conditions by mixing a catalyst (such as 4-toluenesulfonic acid monohydrate) in a proportion of from 0.01 to 10 parts by mass and the solvent in a proportion of from 0 to 5,000 parts by mass, to 100 parts by mass in a total amount of the above starting material and the compound having an R$^F$ group with at most 6 carbon atoms.

As the reaction conditions, preferably, conditions such as reaction container: made of glass, made of SUS, etc., temperature: from 50 to 150° C., pressure: from −0.1 to 1 MPa, atmosphere: gas substitution by nitrogen, argon or the like, time: from 1 to 100 hours, etc. may be mentioned. Further, it is preferred to carry out the reaction, while distilling reaction byproducts off, as the case requires.

A method for purifying the compound (A) from the reaction crude liquid containing the compound (A) thus obtained, may, for example, be a method of distilling off the excess raw material component from the reaction crude liquid and adding chloroform, 2-butanone or the like to recrystallize the compound (B), or a method of distilling off the excess raw material component from the reaction crude liquid, adding dichloropentafluoropropane, chloroform, ethyl acetate or the like thereto, washing the liquid with a sufficient amount of distilled water several times, and then distilling off the solvent.

<Reaction 2>

A mixture of a compound (B1) or a compound (B2) is obtained by reacting an epoxy compound to the compound (A) obtained in the above reaction 1, as shown by the following reaction formula.

HOPhCOO(CH$_2$)$_m$C$_r$F$_{2r+1}$+

→HOCHR$^1$CH$_2$OPhCOO(CH$_2$)$_m$C$_r$F$_{2r+1}$ (B1)

+HOCH$_2$CHR$^1$OPhCOO(CH$_2$)$_m$C$_r$F$_{2r+1}$ (B2)

In the reaction 2, it is preferred to use, as a catalyst, an acid such as hydrochloric acid or sulfuric acid or an alkali such as triethylamine, potassium carbonate or sodium hydroxide. Usually, in a case where an acid is used as the catalyst, the ratio of formulation of the compound (B1) to the compound (B2) is from 20:80 to 80:20, and in a case where an alkali is used as the catalyst, the ratio of formation of the compound (B1) to the compound (B2) is from 100:0 to 90:10. The reaction 2 is preferably carried out in a solvent, and such a solvent may, for example, be specifically DMF, acetonitrile, acetone, 2-butanone, tert-butanol or water.

Specifically, the reaction 2 is carried out under the following preferred reaction conditions, by mixing an acid (such as hydrochloric acid) or an alkali (such as potassium carbonate) in a proportion of from 0.01 to 100 parts by mass and the solvent in a proportion of from 50 to 5,000 parts by mass, to 100 parts by mass in a total amount of the compound (A) and the epoxy compound.

As the reaction conditions, preferably, conditions such as reaction container: made of glass, made of SUS, etc., temperature: from 0 to 150° C., pressure: from 0 to 1 MPa, atmosphere: gas substitution by nitrogen, argon or the like, time: from 1 to 100 hours, etc. may be mentioned.

In the reaction 2, each of the compound (A) and the compounds (B1) and (B2) as reaction products has an ester bond and a hydroxy group, and accordingly depending upon the reaction conditions, an ester exchange reaction of the hydroxy group and the ester bond in such a compound may occur, to form a complicated product. The formed product obtained by such an ester exchange reaction also has both hydroxy group and R$^f$ group, and in the following reaction 3, it is converted to a (meth)acrylate. As a method of suppressing formation of a product by the ester exchange reaction, a method of suppressing the reaction inversion rate to be at most 95% may, for example, be mentioned, and in a case where this method is employed, at least 5% of the compound (A) will remain. The remaining compound (A) has both hydroxy group and the R$^f$ group in the same manner as the above-described product by the ester exchange reaction, and in the reaction 3, it is converted to a (meth)acrylate. The remaining compound (A) can be removed, for example, by column chromatography.

A method for purifying the compound (B1) or the compound (B2) from the reaction crude liquid containing the compound (B1) or (B2) thus obtained, may, for example, be a method of washing the reaction crude liquid with a sufficient amount of distilled water several times, and distilling off the solvent.

Each of the compounds (B1) and (B2) can be isolated from a mixture thereof e.g. by column chromatography, however, from the production viewpoint, they are preferably used as a mixture.

<Reaction 3>

The fluorinated compound (I) or (i') of the present invention is obtained by reacting a (meth)acrylic acid compound to the compound (B1) or (B2) obtained in the above reaction 2, as shown by the following reaction formula:

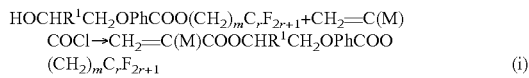

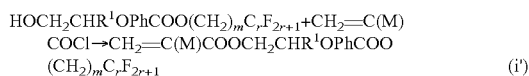

In the above reaction 3, as an alkali, triethylamine, potassium carbonate, sodium hydroxide or the like is used. The reaction 3 is preferably carried out in a solvent, and such a solvent may, for example, be specifically methylene chloride, chloroform, acetone, 2-butanone, ethyl acetate, pyridine or water.

Specifically, the reaction 3 is carried out under the following preferred reaction conditions by mixing the alkali (such as triethylamine) in a proportion of from 25 to 100 parts by mass and the solvent in a proportion of from 50 to 5,000 parts by mass, and further, as the case requires, a suitable amount of the polymerization inhibitor such as hydroquinone, to 100 parts by mass in total of the above compound (B1) or (B2) and the (meth)acrylic acid compound. In a case where the solvent is pyridine, pyridine serves as an alkali, and therefore, it is not necessary to add an alkali. In a case where the solvent is water (Schotten-Baumann reaction), a catalyst such as N-methylimidazole or 4-(dimethylamino) pyridine may be used, as the case requires.

As the reaction conditions, preferably, conditions such as reaction container: made of glass, made of SUS, etc., temperature: from 0 to 80° C., pressure: from 0 to 1 MPa, atmosphere: gas substitution by nitrogen, argon or the like, time: from 1 to 24 hours, etc. may be mentioned.

A method for purifying the fluorinated compound (i) or (i') from the reaction crude liquid containing the fluorinated compound (i) or (I') thus obtained, may, for example, be a method of washing the reaction crude liquid with a sufficient amount of distilled water several times, and distilling off the solvent.

<Polymer of the Present Invention>

The polymer of the present invention is a polymer having structural units based on at least one fluorinated compound selected from the fluorinated compounds (I) of the present invention.

In a case where the polymer of the present invention has structural units based on two or more types of fluorinated compounds (I), it is preferred to polymerize a mixture of the fluorinated compounds (I) wherein X is CHR$^1$CH$_2$O and CH$_2$CHR$^1$O, from the production viewpoint.

The polymer of the present invention may further have structural units based on a compound other than the fluorinated compound (I). In a case where the polymer of the present invention is a polymer based on a plural types of monomers, the proportion of the fluorinated compound (I) is preferably at least 40 mass %, more preferably at least 60 mass %, particularly preferably from 80 to 100 pass % to the structural units (100 mass %) based on all the monomers.

The polymer of the present invention preferably has a mass average molecular weight (Mw) of from 2,000 to 1,000,000, more preferably from 5,000 to 500,000. The polymer having a mass average molecular weight (Mw) within such a range is advantageous from the viewpoint of the durability of the water/oil repellency.

Here, the mass average molecular weight (Mw) of the polymer in this specification is a molecular weight calculated as a polymethyl methacrylate, which is measured by gel permeation chromatography (GPC).

As a method for polymerizing the fluorinated compound of the present invention, it is possible to employ a polymerization method such as an ion polymerization method or a radical polymerization. Particularly, a radical polymerization method is preferred in that the polymerization can be carried out under a mild condition by using a radical initiator as the polymerization initiator. Specifically, the radical polymerization can be carried out by using a polymerization method such as suspension polymerization, solution polymerization, bulk polymerization or emulsion polymerization.

Among these polymerization methods, in the production of the polymer according to the present invention, it is preferred to employ a polymerization method wherein the polymerization is carried out in a medium in the presence of a polymerization initiator, and a solution polymerization employing a solvent as the above medium, or an emulsion polymerization to be carried out by using a medium containing a surfactant and water, is more preferably used.

The production of the polymer is specifically one to polymerize the monomer in a medium in the presence of a polymerization initiator.

Further, in the production of the polymer, the monomer concentration in the medium is preferably from 5 to 50 vol %, more preferably from 20 to 40 vol %, by volume percentage of the monomer to the medium. As the medium, a halogen compound, a hydrocarbon, a ketone, an ester or an ether may, for example, be mentioned.

As the halogen compound, a halogenated hydrocarbon or a halogenated ether may, for example, be mentioned. As the halogenated hydrocarbon, a hydrochlorofluorocarbon or a hydrofluorocarbon may, for example, be mentioned.

As the hydrochlorofluorocarbon, CH$_3$CCl$_2$F, CHCl$_2$CF$_2$CF$_3$ or CHClFCF$_2$CClF$_2$ may, for example, be mentioned.

As the hydrofluorocarbon, CF$_3$CHFCHFCF$_2$CF$_3$, CF$_3$(CF$_2$)$_4$CHF$_2$, CF$_3$CF$_2$CF$_2$CH$_2$CH$_2$CH$_3$, CF$_3$(CF$_2$)$_5$CH$_2$CH$_3$ or 1,1,2,2,3,3,4-heptafluorocyclopentane may, for example, be mentioned.

As the halogenated ether, a hydrofluoroether may, for example, be mentioned.

As the hydrofluoroether, $CF_3CF_2CF_2CF_2OCH_3$, $(CF_3)_2CFCF_2OCH_3$, $CF_3CF_2CF_2CF_2OCH_2CH_3$, $(CF_3)CFCF_2OCH_2CH_3$, $CF_3CF_2CF(OCH_3)CF(CF_3)_2$, $CF_3CF_2CF(OCH_2CH_3)CF(CF_3)_2$, $C_3H_7OCF(CF_3)CF_2OCH_3$, $CHF_2CF_2OCH_2CF_3$ or $CF_3CF_2CH_2OCF_2CHF_2$ may, for example, be mentioned.

As the hydrocarbon, an aliphatic hydrocarbon, an alicyclic hydrocarbon or an aromatic hydrocarbon may, for example, be mentioned.

As the aliphatic hydrocarbon, pentane, 2-methylbutane, 3-methylpentane, hexane, 2,2-dimethylbutane, 2,3-dimethylbutane, heptane, octane, 2,2,4-trimethylpentane, 2,2,3-trimethylhexane, decane, undecane, dodecane, 2,2,4,6,6-pentamethylheptane, tridecane, tetradecane or hexadecane may, for example, be mentioned.

As the alicyclic hydrocarbon, cyclopentane, methylcyclopentane, cyclohexane, methylcyclohexane or ethylcyclohexane may, for example, be mentioned.

As the aromatic hydrocarbon, benzene, toluene or xylene may, for example, be mentioned.

As the ketone, acetone, methyl ethyl ketone, 2-pentanone, 3-pentanone, 2-hexanone or methyl isobutyl ketone may, for example, be mentioned.

As the ester, methyl acetate, ethyl acetate, butyl acetate, methyl propionate, methyl lactate, ethyl lactate or pentyl lactate may, for example, be mentioned.

As the ether, diisopropyl ether, dioxane or tetrahydrofuran may, for example, be mentioned.

As the radical polymerization initiator, a commonly used initiator such as an azo type polymerization initiator, a peroxide type polymerization initiator or a redox type initiator may be used depending upon the polymerization temperature. As the radical polymerization initiator, an azo type compound is particularly preferred, and in a case where the polymerization is carried out in an aqueous medium, a salt of an azo type compound is more preferred.

The amount of the polymerization initiator to be added is preferably from 0.05 to 5 parts by mass, more preferably from 0.1 to 3 parts by mass, per 100 parts by mass of the monomer.

At the time of polymerization of a monomer, a molecular weight-adjusting agent may be used. As the molecular weight-adjusting agent, an aromatic compound, a mercapto alcohol or a mercaptan is preferred, and an alkyl mercaptan is particularly preferred. As such a molecular weight-adjusting agent, specifically, mercapto ethanol, n-octyl mercaptan, n-dodecyl mercaptan, t-dodecyl mercaptan or stearyl mercaptan may, for example, be mentioned.

The amount of the molecular weight-adjusting agent to be added is preferably from 0.01 to 5 parts by mass, more preferably from 0.1 to 3 parts by mass, per 100 parts by mass of the monomer.

The polymerization temperature is preferably from 20 to 150° C. As other polymerization conditions, conditions similar to ones used for polymerization for a usual (meth)acrylate type polymer may be applied. For example, the polymerization may be carried out in a nitrogen atmosphere, or an operation such as shaking may be added, such being preferred conditions in the production method of the present invention. With respect to the polymerization time, the polymer of the present invention can be obtained by carrying out the polymerization for from about 2 to 24 hours, although it may depend also on other polymerization conditions such as the polymerization temperature.

Further, in order to obtain the polymer of the present invention to have the above-mentioned preferred molecular weight range i.e. a range of from 2,000 to 1,000,000, more preferably from 5,000 to 500,000, by mass average molecular weight (Mw), the conditions such as the monomer concentration, the amount of the polymerization initiator, the polymerization temperature, the amount of the molecular weight-adjusting agent, etc. may be adjusted within the above-described preferred ranges. In general, under such a polymerization condition that the monomer concentration is high (low), the amount of the polymerization initiator is small (large), the polymerization temperature is low (high) or the amount of the molecular weight-adjusting agent is small (large), the molecular weight tends to be large (small).

Although the reason is not clearly understood, in the polymer of the present invention, $R^F$ groups are surface-oriented on the surface of a coating film by an interaction due to $\pi$-$\pi$ stacking of a benzene ring contained in the linking group of the fluorinated compound by using the fluorinated compound of the present invention as the monomer. By the surface orientation of $R^F$ groups, even by a monomer having an $R^F$ group with at most 6 carbon atoms, it is possible to impart a high water/oil repellency.

EXAMPLES

Now, Examples of the present invention will be given, but it should be understood that the present invention is by no means restricted by such Examples.

<1> Production of Fluorinated Compound

Example 1

Into a reactor (internal capacity: 500 mL, made of glass) equipped with a stirrer, 4-hydroxybenzoic acid (135.0 g), 4-toluenesulfonic acid monohydrate (9.30 g) and $C_6F_{13}CH_2CH_2OH$ (533.8 g) were put and stirred. Then, heating was carried out so that the internal temperature of the reactor became 140° C., and stirring was further continued for 6 hours while the pressure in the reactor was reduced (from 0 to −0.05 MPa) to distilled off water. The internal temperature of the reactor was decreased to 110° C., and the pressure was further reduced to distill off the excess $C_6F_{13}CH_2CH_2OH$.

The obtained white solid was dissolved in 900 mL of ethyl acetate and put in a separating funnel, followed by washing twice with deionized water (1,200 mL), and the solvent in the ethyl acetate phase was distilled off to obtain 460.8 g of the following compound (A-1) (white solid). The yield was 98%.

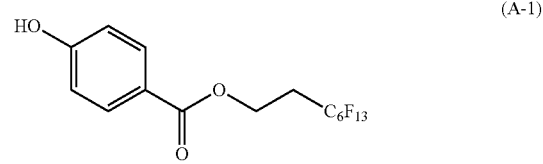

(A-1)

The measurement results of $^1$H-NMR of the obtained compound (A-1) are shown below. Here, each measured value means a measured value derived from a group shown in ( ) following the measured value, but in a case where this group has a portion defined by [ ], the measured value means a measured value derived from the portion defined by [ ]. Hereinafter, the same applies to all of the measurement results of NMR shown in Examples.

$^1$H-NMR (solvent: $CD_3COCD_3$) δ (ppm): 2.81 (2H, m, —$CH_2CF_2$—), 4.62 (2H, t, —COO[$CH_2$]$CH_2$—), 6.94 (2H, d, Ph), 7.91 (2H, d, Ph), 9.21 (1H, s, —OH)

Into a reactor (internal capacity: 500 mL, made of glass) equipped with a stirrer and a Dimroth condenser, the compound (A-1) (100.0 g), potassium carbonate (2.85 g), propylene oxide (18.0 g) and tert-butanol (300 mL) were put and stirred. Then, heating was carried out so that the internal temperature of the reactor became 85° C., and stirring was continued for 48 hours. On that occasion, the inversion rate of the compound (A-1) by means of $^1$H-NMR was 86%.

The solvent of the obtained reaction crude liquid was concentrated, the reaction crude liquid was put in a separating funnel, 300 mL of ethyl acetate was added, the liquid was washed twice with deionized water (300 mL), and the solvent in the ethyl acetate phase was distilled off to obtain 103.9 g of a mixture (B-1). The purity of the mixture (B-1) by means of $^1$H-NMR was such that the compound (B1-1) was 86 mol %, the compound (B2-1) was 4 mol %, and the compound (A-1) was 10 mol %.

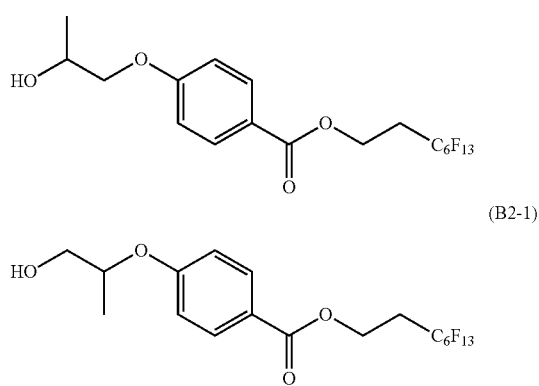

(B1-1)

(B2-1)

The measurement results of $^1$H-NMR of the obtained compound (B1-1) are shown below.

$^1$H-NMR (solvent: CD$_3$COCD$_3$) δ (ppm): 1.25 (3H, d, —CH$_3$), 2.82 (2H, m, —CH$_2$CF$_2$—), 3.98 (2H, d, —CH(CH$_3$)[CH$_2$]—), 4.14 (1H, m, —[CH](CH$_3$)—), 4.64 (2H, t, —COO[CH$_2$]CH$_2$—), 7.05 (2H, d, Ph), 7.97 (2H, d, Ph)

The measurement results of $^1$H-NMR of the obtained compound (B2-1) are shown below.

$^1$H-NMR (solvent: CD$_3$COCD$_3$) δ (ppm): 1.31 (3H, d, —CH$_3$), 2.82 (2H, m, —CH$_2$CF$_2$—), 3.64 (2H, d, —CH(CH$_3$)[CH$_2$]—), 4.62 (1H, m, —[CH](CH$_3$)—), 4.64 (2H, t, —COO[CH$_2$]CH$_2$—), 7.05 (2H, d, Ph), 7.97 (2H, d, Ph)

Into a reactor (internal capacity: 50 mL, made of glass) equipped with a stirrer and a dropping funnel, the mixture (B-1) (7.50 g), triethylamine (1.68 g) and acetone (20 mL) were put and stirred. Then, by an ice bath, the internal temperature of the reactor was adjusted to be at most 10° C., and in a nitrogen atmosphere, acrylic acid chloride (1.38 g) was dropwise added. Further, the temperature was returned to room temperature, and stirring was continued for 15 hours.

The obtained reaction crude liquid was transferred to a separating funnel, 20 mL of dichloropentafluoropropane (manufactured by Asahi Glass Company, Limited, tradename: AK-225) was added, followed by washing three times with distilled water (20 mL), and the solvent in the AK-225 phase was distilled off to obtain 8.20 g of a mixture (C-1). The purity of the mixture (C-1) by means of $^1$H-NMR was such that the compound (I-1) was 86 mol %, the compound (I'-1) was 4 mol %, and the compound (A-2) was 10 mol %.

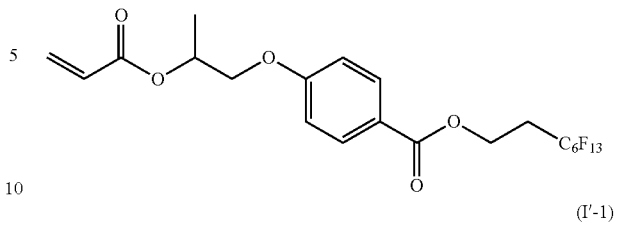

(I-1)

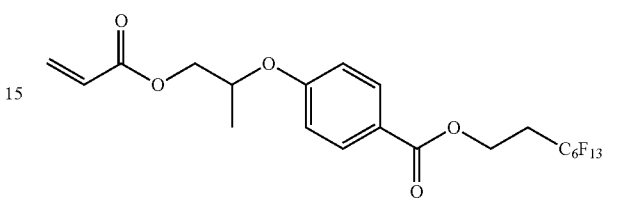

(I'-1)

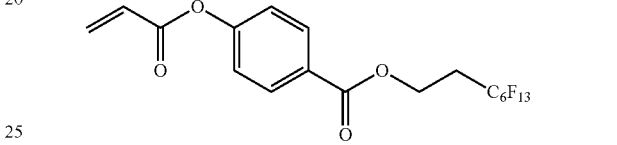

(A-2)

The measurement results of $^1$H-NMR of the obtained compound (I-1) are shown below.

$^1$H-NMR (solvent: CDCl$_3$) δ (ppm): 1.41 (3H, d, —CH$_3$), 2.61 (2H, m, —CH$_2$CF$_2$—), 4.11 (2H, m, —CH(CH$_3$)[CH$_2$]—), 4.61 (2H, t, —COO[CH$_2$]CH$_2$—), 5.33 (1H, m, —[CH](CH$_3$)—), 5.84 (1H, s, transC═CH$_2$), 6.13 (1H, dd, —CH═), 6.42 (1H, s, cisC═CH$_2$), 6.94 (2H, d, Ph), 7.98 (2H, d, Ph)

The measurement results of $^1$H-NMR of the obtained compound (I'-1) are shown below.

$^1$H-NMR (solvent: CDCl$_3$) δ (ppm): 1.47 (3H, d, —CH$_3$), 2.61 (2H, m, —CH$_2$CF$_2$—), 4.27 (2H, m, —CH(CH$_3$)[CH$_2$]—), 4.61 (2H, t, —COO[CH$_2$]CH$_2$—), 4.76 (1H, m, —[CH](CH$_3$)—), 5.84 (1H, s, transC═CH$_2$), 6.13 (1H, dd, —CH═), 6.42 (1H, s, cisC═CH$_2$), 6.94 (2H, d, Ph), 7.98 (2H, d, Ph)

The measurement results of $^1$H-NMR of the obtained compound (A-2) are shown below.

$^1$H-NMR (solvent: CDCl$_3$) δ (ppm): 2.61 (2H, m, —CH$_2$CF$_2$—), 4.63 (2H, t, —COOCH$_2$—), 6.06 (1H, s, transC═CH$_2$), 6.33 (1H, dd, —CH═), 6.63 (1H, s, cisC═CH$_2$), 7.24 (2H, d, Ph), 8.09 (2H, d, Ph)

Example 2

Into a reactor (internal capacity: 50 mL, made of glass) equipped with a stirrer and a Dimroth condenser, the mixture (B-1) (7.30 g) obtained in Example 1, triethylamine (1.63 g) and acetone (20 mL) were put and stirred. Then, by an ice bath, the internal temperature of the reactor was adjusted to be at most 10° C., and in a nitrogen atmosphere, methacrylic acid chloride (1.55 g) was dropwise added. Further, the temperature was returned to room temperature, and stirring was continued for 15 hours.

The obtained reaction crude liquid was transferred to a separating funnel, 20 mL of AK-225 was added, followed by washing three times with distilled water (20 mL), and the solvent in the AK-225 phase was distilled off to obtain 8.20 g of a mixture (C-2). The purity of the mixture (C-2) by means of $^1$H-NMR was such that the compound (I-2) was 83 mol %, the compound (I'-2) was 8 mol %, and the compound (A-3) was 9 mol %.

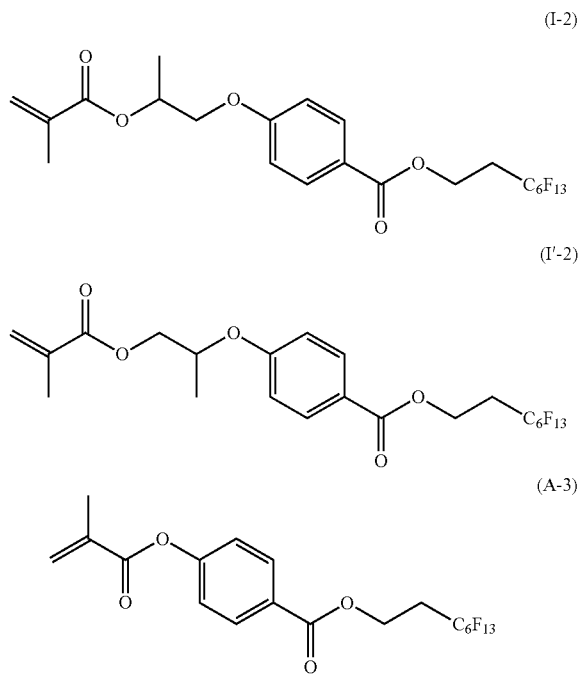

The measurement results of $^1$H-NMR of the obtained compound (I-2) are shown below.

$^1$H-NMR (solvent: CDCl$_3$) δ (ppm): 1.41 (3H, d, —CH([CH$_3$])—), 1.94 (3H, s, —C(CH$_3$)═), 2.60 (2H, m, —CH$_2$CF$_2$—), 4.11 (2H, m, —CH(CH$_3$)[CH$_2$]—), 4.60 (2H, t, —COO[CH$_2$]CH$_2$—), 5.32 (1H, m, —[CH](CH$_3$)—), 5.57 (1H, s, transC═CH$_2$), 6.10 (1H, s, cisC═CH$_2$), 6.94 (2H, d, Ph), 7.99 (2H, d, Ph)

The measurement results of $^1$H-NMR of the obtained compound (I'-2) are shown below.

$^1$H-NMR (solvent: CDCl$_3$) δ (ppm): 1.47 (3H, d, —CH$_3$), 1.91 (3H, s, —C(CH$_3$)═), 2.61 (2H, m, —CH$_2$CF$_2$—), 4.27 (2H, m, —CH(CH$_3$)[CH$_2$]—), 4.61 (2H, t, —COO[CH$_2$]CH$_2$—), 4.76 (1H, m, —[CH](CH$_3$)—), 5.57 (1H, s, transC═CH$_2$), 6.10 (1H, s, cisC═CH$_2$), 6.94 (2H, d, Ph), 7.98 (2H, d, Ph)

The measurement results of $^1$H-NMR of the obtained compound (A-3) are shown below.

$^1$H-NMR (solvent: CDCl$_3$) δ (ppm): 2.07 (3H, s, CH$_3$—), 2.61 (2H, m, —CH$_2$CF$_2$—), 4.63 (2H, t, —COOCH$_2$—), 5.80 (1H, s, transC═CH$_2$), 6.38 (1H, s, cisC═CH$_2$), 7.23 (2H, d, Ph), 8.08 (2H, d, Ph)

Example 3

Into a reactor (internal capacity: 300 mL, made of glass) equipped with a stirrer and a Dimroth condenser, the compound (A-1) (46.0 g) obtained in Example 1, potassium carbonate (3.14 g), butylene oxide (20.6 g) and tert-butanol (150 mL) were put and stirred. Then, heating was carried out so that the internal temperature of the reactor became 85° C., and stirring was continued for 20 hours. On that occasion, the inversion rate of the compound (A-1) by means of $^1$H-NMR was 90%.

The solvent in the obtained reaction crude liquid was concentrated, the reaction crude liquid was transferred to a separating funnel, 200 mL of ethyl acetate was added, followed by washing twice with deionized water (200 mL), and the solvent in the ethyl acetate phase was distilled off to obtain 38.4 g of a mixture (B-2). The purity of the mixture (B-2) by means of $^1$H-NMR was such that the compound (B1-2) was 84 mol %, the compound (B2-2) was 6 mol %, and the compound (A-1) was 10 mol %.

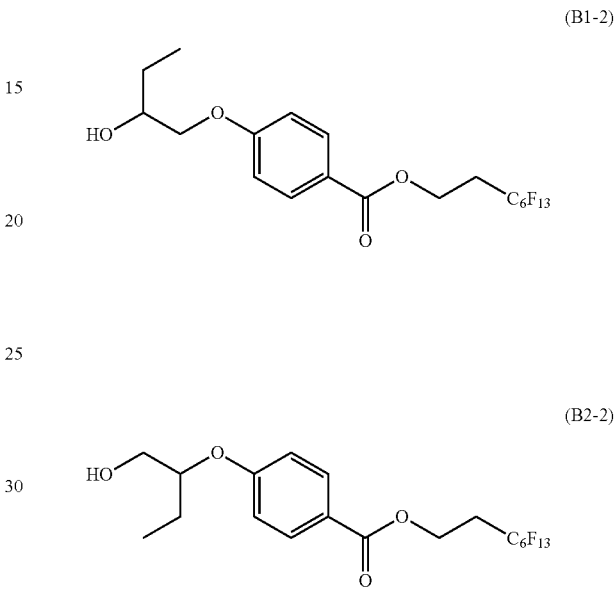

The measurement results of $^1$H-NMR of the obtained compound (B1-2) are shown below.

$^1$H-NMR (solvent: CDCl$_3$) δ (ppm): 1.05 (3H, t, —CH$_3$), 1.64 (2H, m, —[CH$_2$]CH$_3$), 2.25 (1H, s, —OH), 2.60 (2H, m, —CH$_2$CF$_2$—), 3.96 (3H, m, —[CH](CH$_2$CH$_3$)[CH$_2$]—), 4.60 (2H, t, —COO[CH$_2$]CH$_2$—), 6.94 (2H, d, Ph), 7.99 (2H, d, Ph)

The measurement results of $^1$H-NMR of the obtained compound (B2-2) are shown below.

$^1$H-NMR (solvent: CDCl$_3$) δ (ppm): 1.05 (3H, t, —CH$_3$), 1.86 (2H, m, —[CH$_2$]CH$_3$), 2.25 (1H, s, —OH), 2.60 (2H, m, —CH$_2$CF$_2$—), 3.96 (2H, m, —CH(CH$_2$CH$_3$)[CH$_2$]—), 4.19 (1H, m, —[CH](CH$_2$CH$_3$)CH$_2$—), 4.60 (2H, t, —COO[CH$_2$]CH$_2$—), 6.94 (2H, d, Ph), 7.99 (2H, d, Ph)

Into a reactor (internal capacity: 50 mL, made of glass) equipped with a stirrer and a dropping funnel, the mixture (B-2) (18.0 g), triethylamine (3.93 g) and acetone were put and stirred. Then, by an ice bath, the internal temperature of the reactor was adjusted to be at most 10° C., and in a nitrogen atmosphere, acrylic acid chloride (3.22 g) was dropwise added. Further, the temperature was returned to room temperature, and stirring was continued for 15 hours.

The obtained reaction crude liquid was transferred to a separating funnel, 50 mL of AK-225 was added, followed by washing three times with distilled water (50 mL), and the solvent in the AK-225 layer was distilled off to obtain 19.1 g of a mixture (C-3). The purity of the mixture (C-3) by means of $^1$H-NMR was such that the compound (I-3) was 86 mol %, the compound (I'-3) was 4 mol %, and the compound (A-2) was 10 mol %.

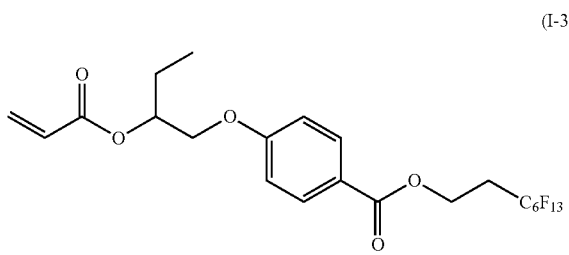

(I-3)

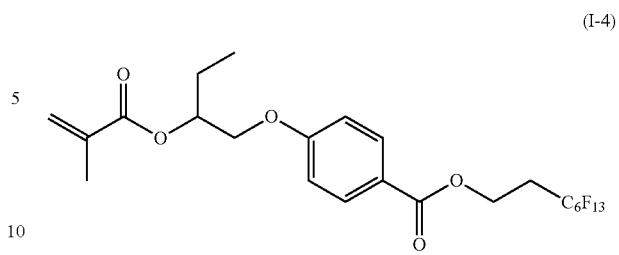

(I-4)

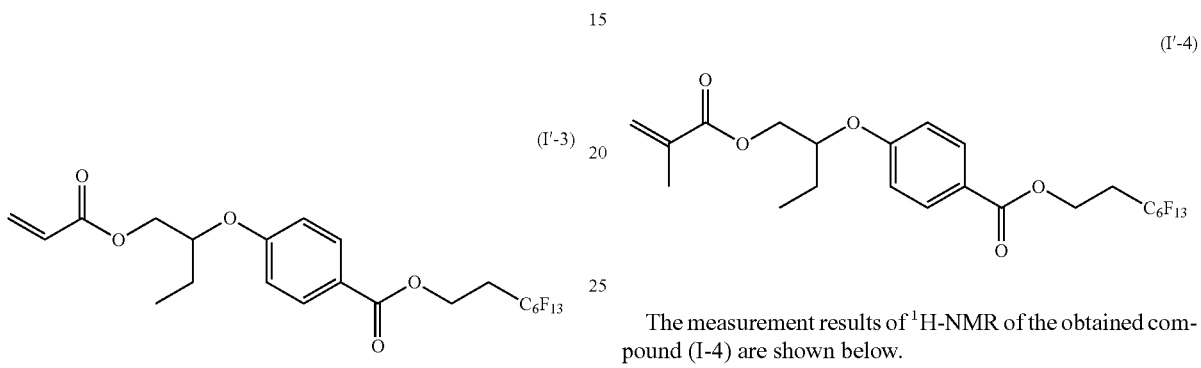

(I'-3)

(I'-4)

The measurement results of ¹H-NMR of the obtained compound (I-3) are shown below.

¹H-NMR (solvent: CDCl₃) δ (ppm): 0.99 (3H, t, —CH₃), 1.82 (2H, m, —[CH₂]CH₃), 2.60 (2H, m, —CH₂CF₂—), 4.12 (2H, m, —CH(CH₂CH₃)[CH₂]—), 4.60 (2H, t, —COO[CH₂]CH₂—), 5.23 (1H, m, —[CH](CH₂CH₃)CH₂—), 5.85 (1H, s, transC=CH₂), 6.14 (1H, dd, —CH=), 6.43 (1H, s, cisC=CH₂), 6.93 (2H, d, Ph), 7.98 (2H, d, Ph)

The measurement results of ¹H-NMR of the obtained compound (I'-3) are shown below.

¹H-NMR (solvent: CDCl₃) δ (ppm): 1.04 (3H, t, —CH₃), 1.82 (2H, m, —[CH₂]CH₃), 2.60 (2H, m, —CH₂CF₂—), 4.37 (2H, m, —CH(CH₂CH₃)[CH₂]—), 4.43 (1H, m, —[CH](CH₂CH₃)CH₂—), 4.60 (2H, t, —COO[CH₂]CH₂—), 5.85 (1H, s, transC=CH₂), 6.14 (1H, dd, —CH=), 6.43 (1H, s, cisC=CH₂), 6.93 (2H, d, Ph), 7.98 (2H, d, Ph)

Example 4

Into a reactor (internal capacity: 50 mL, made of glass) equipped with a stirrer and a dropping funnel, the mixture (B-2) (18.0 g) obtained in Example 3, triethylamine (3.93 g) and acetone (40 mL) were put and stirred. Then, by an ice bath, the internal temperature of the reactor was adjusted to be at most 10° C., and in a nitrogen atmosphere, methacrylic acid chloride (3.73 g) was dropwise added. Further, the temperature was returned to room temperature, and stirring was continued for 15 hours.

The obtained reaction crude liquid was transferred to a separating funnel, 50 mL of AK-225 was added, followed by washing three times with distilled water (50 mL), and the solvent in the AK-225 phase was distilled off to obtain 10.6 g of a mixture (C-4). The purity of the mixture (C-4) by means of ¹H-NMR was such that the compound (I-4) was 84 mol %, the compound (I'-4) was 3 mol %, and the compound (A-3) was 13 mol %.

The measurement results of ¹H-NMR of the obtained compound (I-4) are shown below.

¹H-NMR (solvent: CDCl₃) δ (ppm): 1.00 (3H, t, —CH₂[CH₃]), 1.83 (2H, m, —[CH₂]CH₃), 1.95 (3H, s, —C(CH₃)=), 2.59 (2H, m, —CH₂CF₂—), 4.13 (2H, m, —CH(CH₂CH₃)[CH₂]—), 4.60 (2H, t, —COO[CH₂]CH₂—), 5.20 (1H, m, —[CH](CH₂CH₃)CH₂—), 5.57 (1H, s, transC=CH₂), 6.12 (1H, s, cisC=CH₂), 6.94 (2H, d, Ph), 7.98 (2H, d, Ph)

The measurement results of ¹H-NMR of the obtained compound (I'-4) are shown below.

¹H-NMR (solvent: CDCl₃) δ (ppm): 1.00 (3H, t, —CH₂[CH₃]), 1.83 (2H, m, —[CH₂]CH₃), 1.95 (3H, s, —C(CH₃)=), 2.59 (2H, m, —CH₂CF₂—), 4.32 (2H, m, —CH(CH₂CH₃)[CH₂]—), 4.42 (1H, m, —[CH](CH₂CH₃)CH₂—), 4.60 (2H, t, —COO[CH₂]CH₂—), 5.57 (1H, s, transC=CH₂), 6.10 (1H, s, cisC=CH₂), 6.94 (2H, d, Ph), 7.98 (2H, d, Ph)

Example 5

Into a reactor (internal capacity: 200 mL, made of glass) equipped with a stirrer and a Dimroth condenser, the compound (A-1) (25.0 g) obtained in Example 1, potassium carbonate (0.71 g), tert-butyl glycidyl ether (11.1 g) and tert-butanol (100 mL) were put and stirred. Then, heating was carried out so that the internal temperature of the reactor became 80° C., and stirring was continued for 20 hours. On that occasion, the inversion rate of the compound (A-1) by means of ¹H-NMR was 91%.

The solvent in the obtained reaction crude liquid was concentrated, the reaction crude liquid was transferred to a separating funnel, 100 mL of ethyl acetate was added, followed by washing twice with deionized water (100 mL), and the solvent in the ethyl acetate phase was distilled off to obtain 30.2 g of a mixture (B-3). The purity of the mixture (B-3) by means of ¹H-NMR was such that the compound (B1-3) was 90 mol %, the compound (B2-3) was 2 mol %, and the compound (A-1) was 8 mol %.

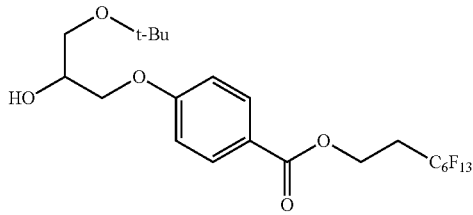

(B1-3)

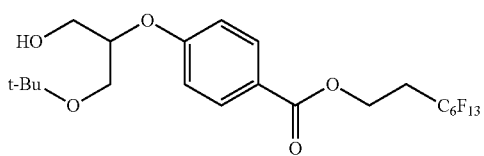

(B2-3)

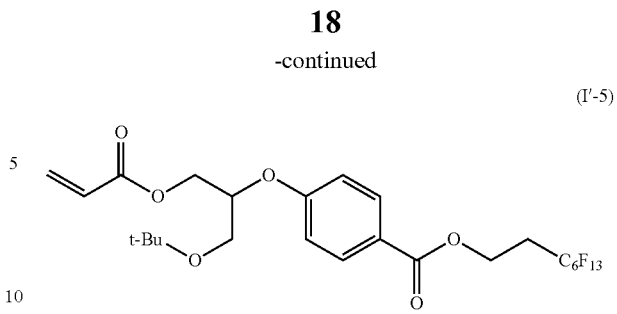

(I'-5)

The measurement results of $^1$H-NMR of the obtained compound (B1-3) are shown below.

$^1$H-NMR (solvent: CDCl$_3$) δ (ppm): 1.21 (9H, s, —C(CH$_3$)$_3$), 2.60 (2H, m, —CH$_2$CF$_2$—), 3.54 (2H, m, —[CH$_2$]OC(CH$_3$)$_3$), 4.07 (3H, m, —[CH](CH$_2$OC(CH$_3$)$_3$)[CH$_2$]—), 4.60 (2H, t, —COO[CH$_2$]CH$_2$—), 6.95 (2H, d, Ph), 7.98 (2H, d, Ph)

The measurement results of $^1$H-NMR of the obtained compound (B2-3) are shown below.

$^1$H-NMR (solvent: CDCl$_3$) δ (ppm): 1.19 (9H, s, —C(CH$_3$)$_3$), 2.60 (2H, m, —CH$_2$CF$_2$—), 3.54 (2H, m, —[CH$_2$]OC(CH$_3$)$_3$), 3.70 (2H, d, —CH(CH$_2$OC(CH$_3$)$_3$)[CH$_2$]—), 4.34 (3H, m, —[CH](CH$_2$OC(CH$_3$)$_3$)CH$_2$—), 4.60 (2H, t, —COO[CH$_2$]CH$_2$—), 6.95 (2H, d, Ph), 7.98 (2H, d, Ph)

Into a reactor (internal capacity: 100 mL, made of glass) equipped with a stirrer and a dropping funnel, the mixture (B-3) (15.0 g), triethylamine (3.46 g) and acetone (40 mL) were put and stirred. Then, by an ice bath, the internal temperature of the reactor was adjusted to be at most 10° C., and in a nitrogen atmosphere, acrylic acid chloride (2.65 g) was dropwise added. Further, the temperature was returned to room temperature, and stirring was continued for 15 hours.

The obtained reaction crude liquid was transferred to a separating funnel, 50 mL of AK-225 was added, followed by washing three times with distilled water (50 mL), and the solvent in the AK-225 phase was distilled off to obtain 15.9 g of a mixture (C-5). The purity of the mixture (C-5) by means of $^1$H-NMR was such that the compound (I-5) was 90 mol %, the compound (I'-5) was 2 mol %, and the compound (A-2) was 8 mol %.

The measurement results of $^1$H-NMR of the obtained compound (I-5) are shown below.

$^1$H-NMR (solvent: CDCl$_3$) δ (ppm): 1.18 (9H, s, —C(CH$_3$)$_3$), 2.63 (2H, m, —CH$_2$CF$_2$—), 3.64 (2H, d, —[CH$_2$]OC(CH$_3$)$_3$), 4.27 (2H, m, —CH(CH$_2$OC(CH$_3$)$_3$)[CH$_2$]—), 4.61 (2H, t, —COO[CH$_2$]CH$_2$—), 5.30 (1H, m, —[CH](CH$_2$OC(CH$_3$)$_3$)CH$_2$—), 5.87 (1H, s, transC=CH$_2$), 6.16 (1H, dd, —CH=), 6.44 (1H, s, cisC=CH$_2$), 6.97 (2H, d, Ph), 7.98 (2H, d, Ph)

The measurement results of $^1$H-NMR of the obtained compound (I'-5) are shown below.

$^1$H-NMR (solvent: CDCl$_3$) δ (ppm): 1.18 (9H, s, —C(CH$_3$)$_3$), 2.63 (2H, m, —CH$_2$CF$_2$—), 3.60 (2H, d, —[CH$_2$]OC(CH$_3$)$_3$), 4.42 (2H, m, —CH(CH$_2$OC(CH$_3$)$_3$)[CH$_2$]—), 4.61 (2H, t, —COO[CH$_2$]CH$_2$—), 4.63 (1H, m, —[CH](CH$_2$OC(CH$_3$)$_3$)CH$_2$—), 5.87 (1H, s, transC=CH$_2$), 6.16 (1H, dd, —CH=), 6.44 (1H, s, cisC=CH$_2$), 6.97 (2H, d, Ph), 7.98 (2H, d, Ph)

Example 6

Into a reactor (internal capacity: 50 mL, made of glass) equipped with a stirrer and a dropping funnel, the mixture (B-3) (15.0 g) obtained in Example 5, triethylamine (3.46 g) and acetone (40 mL) were put and stirred. Then, by an ice bath, the internal temperature of the reactor was adjusted to be at most 10° C., and in a nitrogen atmosphere, methacrylic acid chloride (3.06 g) was dropwise added. Further, the temperature was returned to room temperature, and stirring was continued for 15 hours.

The obtained reaction crude liquid was transferred to a separating funnel, 50 mL of AK-225 was added, followed by washing three times with distilled water (50 mL), and the solvent in the AK-225 phase was distilled off to obtain 15.3 g of a mixture (C-6). The purity of the mixture (C-6) by means of $^1$H-NMR was such that the compound (I-6) was 90 mol %, the compound (I'-6) was 2 mol %, and the compound (A-3) was 8 mol %.

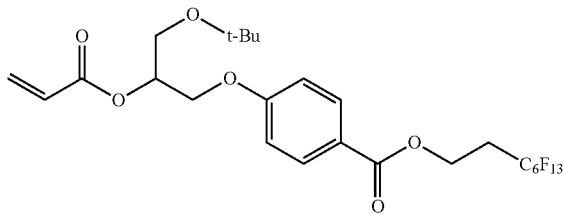

(I-5)

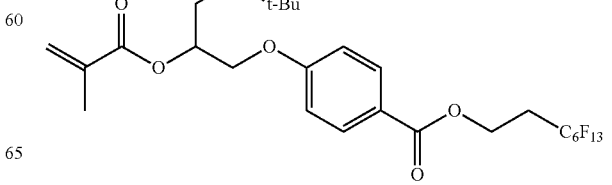

(I-6)

-continued (I'-6)

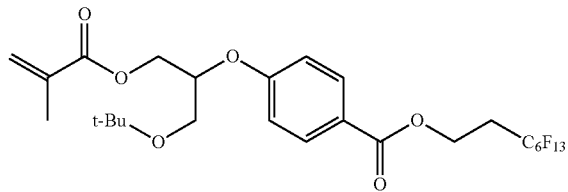

The measurement results of ¹H-NMR of the obtained compound (I-6) are shown below.

¹H-NMR (solvent: CDCl₃) δ (ppm): 1.18 (9H, s, —C(CH₃)₃), 1.94 (3H, s, —C(CH₃)═), 2.60 (2H, m, —CH₂CF₂—), 3.63 (2H, d, —[CH₂]OC(CH₃)₃), 4.27 (2H, m, —CH(CH₂OC(CH₃)₃)[CH₂]—), 4.60 (2H, t, —COO[CH₂]CH₂—), 5.27 (1H, m, —[CH](CH₂OC(CH₃)₃)CH₂—), 5.58 (1H, s, transC═CH₂), 6.13 (1H, s, cisC═CH₂), 6.96 (2H, d, Ph), 7.98 (2H, d, Ph)

The measurement results of ¹H-NMR of the obtained compound (I'-6) are shown below.

¹H-NMR (solvent: CDCl₃) δ (ppm): 1.18 (9H, s, —C(CH₃)₃), 1.94 (3H, s, —C(CH₃)═), 2.63 (2H, m, —CH₂CF₂—), 3.61 (2H, d, —[CH₂]OC(CH₃)₃), 4.41 (2H, m, —CH(CH₂OC(CH₃)₃)[CH₂]—), 4.61 (2H, t, —COO[CH₂]CH₂—), 4.63 (1H, m, —[CH](CH₂OC(CH₃)₃)CH₂—), 5.57 (1H, s, transC═CH₂), 6.10 (1H, s, cisC═CH₂), 6.97 (2H, d, Ph), 7.98 (2H, d, Ph)<

<2> Production of Polymer

Example 7

Using the mixture (C-1) of the fluorinated compound obtained in the above Example 6 as a monomer, a polymer was produced as follows.

Into a 30 mL glass ampoule for polymerization, 3.6 g of the mixture (C-1) as the fluorinated compound, 10 mg of 2,2'-azobisisobutyronitrile as an initiator and 8.4 g of a mixture of AK-225 and tetrahydrofuran (THF) (mass ratio 50:50) as a solvent were put, as shown in Table 1. The gas in the interior of the ampoule was substituted by nitrogen gas, and then, the ampoule was sealed and maintained for 16 hours in a hot bath of 60° C. The solution containing the polymer was dropped into methanol of 20 times by mass, followed by stirring to let solid precipitate. The obtained solid was collected by filtration and vacuum-dried overnight at 60° C. to obtain a polymer in the amount shown by mass in Table 1. The molecular weight of the recovered polymer was measured by GPC. The mass average molecular weight (Mw) of the obtained polymer is shown in Table 1.

Examples 8 to 12

Polymers were obtained in the same manner as in Example 7 except that the mixtures of the fluorinated compound as shown in Table 1 were used as monomers.

The mass (g) and the mass average molecular weight (Mw) of the obtained polymers are shown in Table 1.

Here, the above mass average molecular weight (Mw) was measured by the following GPC measuring method.
(GPC Measuring Method)

The recovered polymer was dissolved in a mixed solvent of a fluorinated solvent (AK-225)/hexafluoroisopropyl alcohol=99/1 (volume ratio) to obtain a 0.5 mass % solution, which was passed through a filter of 0.2 μm to obtain an analytical sample. With respect to such a sample, the number average molecular weight (Mn) and the mass average molecular weight (Mw) were measured. The measuring conditions were as follows.

Apparatus: HLC-8220GPC, manufactured by TOSOH CORPORATION,
Column: Two MIXED-E, manufactured by Polymer Laboratories, were connected in series,
Temperature for measurement: 37° C.,
Amount injected: 50 μL,
Exit velocity: 1 mL/min,
Standard sample: EasiCal PM-2, manufactured by Polymer Laboratories,
Eluent: Mixed solvent of fluorinated solvent (AK-225)/hexafluoroisopropyl alcohol=99/1 (volume ratio).

TABLE 1

| Ex. No. | Mixture Symbol | Polymer Yield (g) | Mw |
|---|---|---|---|
| Ex. 7 | C-1 | 2.6 | 15,500 |
| 8 | C-2 | 3.3 | 194,500 |
| 9 | C-3 | 3.5 | 189,900 |
| 10 | C-4 | 3.2 | 98,600 |
| 11 | C-5 | 3.5 | 137,600 |
| 12 | C-6 | 3.2 | 92,700 |

<Evaluation>

With respect to each of the polymers obtained in Examples 7 to 12, a test plate was prepared by the following method, and the water/oil repellency was evaluated. The results are shown in Table 2.

[Preparation of Test Plate]

A obtained polymer was diluted with AK-225 so that the solid content concentration became 2.0 mass %, and the obtained polymer solution was used as a treating liquid. The polymer solution was applied by dip coating to three glass plates and dried at 150° C. for 10 minutes to obtain treated substrates each having a coating film formed on the surface.

[Water/Oil Repellency]

Using one of the above treated substrates, the contact angles of water and hexadecane on the coating film were measured, whereby the water/oil repellency of the coating film obtainable from the treating liquid containing the polymer prepared in each of the above Examples, was evaluated. Here, the measurements of the contact angles were carried out by means of CA-X, manufactured by Kyowa Interface Science Co., Ltd.

As results, the actually measured values of the contact angles as well as the results evaluated in accordance with the following standards, are shown.

The water repellency was evaluated by three grades using the contact angle of water being 100° as the standard.

⊚ (contact angle: at least 110°): Excellent in water repellency
○ (contact angle: at least 100° and less than 110°): Water repellency observed
X (contact angle: less than 100°): Inadequate in water repellency The oil repellency was evaluated by three grades using the contact angle of n-hexadecane being 60° as the standard.

⊚ (contact angle: at least 70°): Excellent in oil repellency
○ (contact angle: at least 60° and less than 70°): Oil repellency observed X (contact angle: less than 60°): Inadequate in oil repellency

[Dynamic Water Repellency]

Using one of the above treated substrates, the dynamic contact angles to water on the coating film was measured, whereby the dynamic water repellency of the coating film obtainable from the treating liquid containing a polymer prepared in each of the above Examples, was evaluated. Here, by means of DCAT21 (manufactured by DataPhysics), the receding contact angle to water was measured at 25° C. by Wilhelmy method. As results, the actually measured values of the receding contact angles as well as the results evaluated in accordance with the following standards, are shown.

The dynamic water repellency was evaluated by three grades using the receding contact angle of water being 70° as the standard.

⊚ (contact angle: at least 80°): Excellent in dynamic water repellency

○ (contact angle: at least 70° and less than 80°): Dynamic water repellency observed X (contact angle: less than 70°): Inadequate in dynamic water repellency

[Durability]

Using one of the above treated substrates, such a substrate was immersed for 3 hours in distilled water of 40° C., and the dynamic contact angle was measured, whereupon from the change rate between the receding contact angle where no treatment was carried out and the receding contact angle after the treatment, the durability of the dynamic water repellency of the coating film was evaluated. As results, the actually measured values of the receding contact angles after the immersion as well as the results evaluated in accordance with the following standards, are shown.

⊚ (change rate: less than 20%): Excellent in durability of dynamic water repellency ○ (change rate: at least 20% and less than 50%): Durability in dynamic water repellency observed X (change rate: at least 50%): Inadequate in durability of dynamic water repellency

INDUSTRIAL APPLICABILITY

The fluorinated compound of the present invention is a fluorinated compound having an $R^F$ group with at most 6 carbon atoms, which presents little environmental load, and a polymer obtainable by polymerizing it has a highly durable water/oil repellency. Accordingly, in place of a copolymer having an $R^F$ group with at least 8 carbon atoms presenting a high environmental load, it is useful for e.g. a water/oil repellent composition.

This application is a continuation of PCT Application No. PCT/JP2011/058321 filed on Mar. 31, 2011, which is based upon and claims the benefit of priority from Japanese Patent Application No. 2010-085028 filed on Apr. 1, 2010. The contents of those applications are incorporated herein by reference in its entirety.

What is claimed is:

1. A fluorinated compound represented by the following formula (I):

$$CH_2=C(M)COOXPhCOO(CH_2)_m C_r F_{2r+1} \quad (I)$$

(in the formula (I), M is a hydrogen atom, a methyl group or a halogen atom, X is $CHR^1CH_2O$ or $CH_2CHR^1O$, $R^1$ is a $C_{1-4}$ linear or branched alkyl group or $CH_2OR^2$, $R^2$ is a $C_{1-4}$ linear or branched alkyl group, Ph is a phenylene group, m is an integer of from 1 to 4, and r is an integer of from 1 to 6).

2. The fluorinated compound according to claim 1, wherein Ph in the formula (I) is a 1,4-phenylene group.

3. The fluorinated compound according to claim 1, wherein r in the formula (I) is an integer of from 2 to 6.

4. The fluorinated compound according to claim 3, wherein r in the formula (I) is an integer of from 4 to 6.

5. The fluorinated compound according to claim 1, wherein the fluorinated compound represented by the formula (I) is a compound represented by any one of the following formulae (I-1) to (I-6) and (I'-1) to (I'-6):

TABLE 2

| | | Water/oil repellency | | | Dynamic water repellency | | | |
| | | | | | Receding | | Receding | |
| Ex. No. | | Contact angle (water) | Evaluation of water repellency | Contact angle (hexadecane) | Evaluation of oil repellency | contact angle (initial) | Evaluation of water repellency | contact angle (after immersion) | Evaluation of durability |
|---|---|---|---|---|---|---|---|---|---|
| Ex. | 7 | 115 | ⊚ | 75 | ⊚ | 80 | ⊚ | 68 | ⊚ |
| | 8 | 112 | ⊚ | 72 | ⊚ | 93 | ⊚ | 60 | ○ |
| | 9 | 112 | ⊚ | 70 | ⊚ | 70 | ○ | 57 | ⊚ |
| | 10 | 110 | ⊚ | 69 | ○ | 87 | ⊚ | 67 | ○ |
| | 11 | 110 | ⊚ | 68 | ○ | 71 | ○ | 41 | ○ |
| | 12 | 108 | ○ | 68 | ○ | 81 | ⊚ | 65 | ⊚ |

As is evident from Table 2, it is possible to obtain a polymer having a highly durable water/oil repellency by using the fluorinated compound of the present invention.

Further, from the results, it can be said that in a case of the fluorinated compound of the present invention of the formula (I) wherein M is a hydrogen atom, the obtainable polymer has water/oil repellency and is excellent in durability for maintaining such water/oil repellency. Further, in the case of the fluorinated compound of the present invention of the formula (I) wherein M is a methyl group, the obtainable polymer is particularly excellent in the initial water/oil repellency and excellent also in the durability for maintaining it.

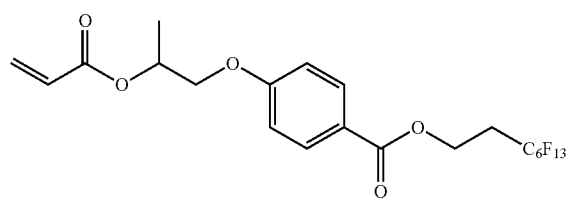

(I-1)

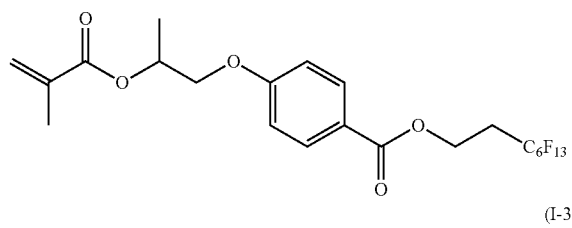
(I-2)
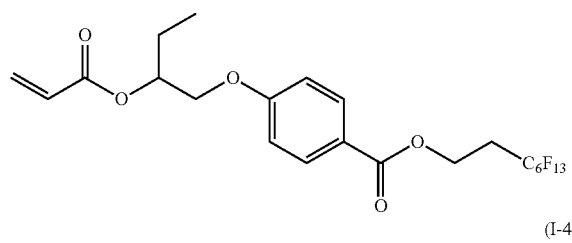
(I-3)
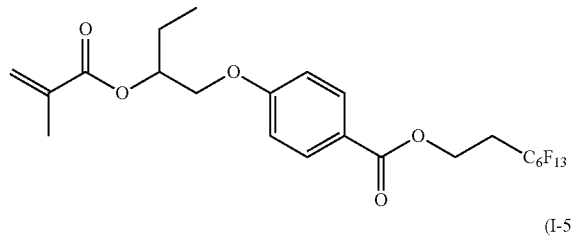
(I-4)
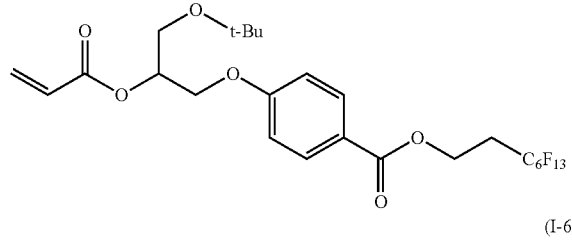
(I-5)
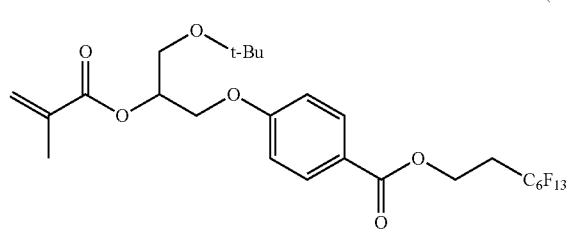
(I-6)
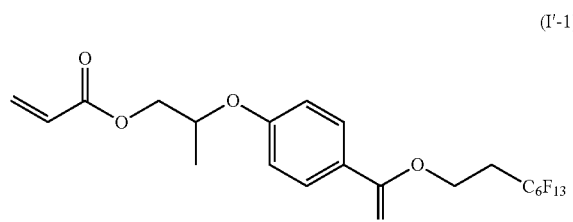
(I'-1)
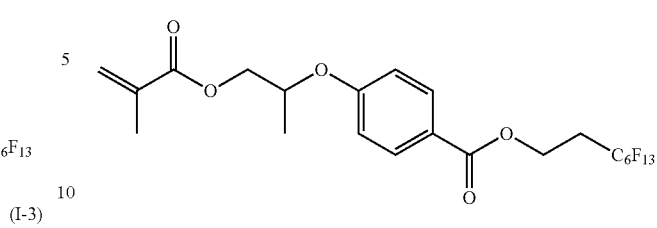
(I'-2)
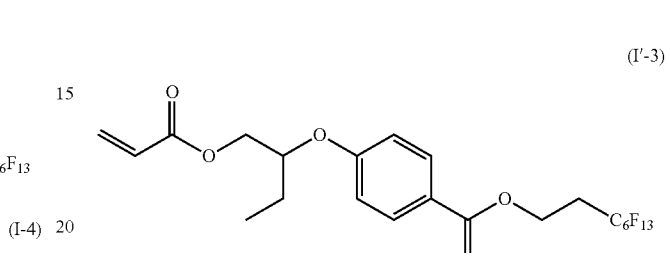
(I'-3)
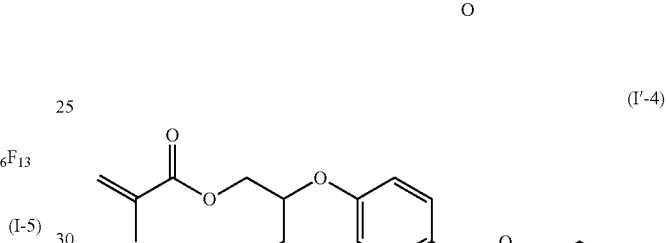
(I'-4)
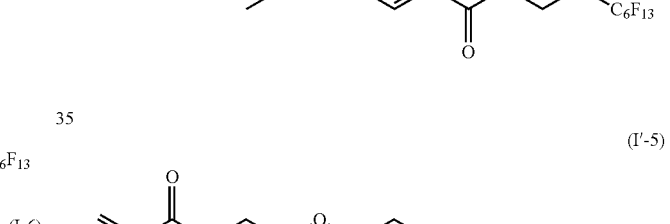
(I'-5)
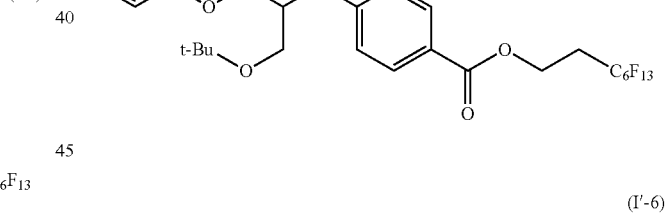
(I'-6)
* * * * *